(12) United States Patent
Fattori

(10) Patent No.: US 9,795,465 B2
(45) Date of Patent: Oct. 24, 2017

(54) ORAL CARE IMPLEMENT AND REFILL HEAD THEREFOR

(75) Inventor: Joseph E. Fattori, East Sandwich, MA (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 700 days.

(21) Appl. No.: 14/344,877

(22) PCT Filed: Sep. 13, 2012

(86) PCT No.: PCT/US2012/054998
§ 371 (c)(1),
(2), (4) Date: Mar. 13, 2014

(87) PCT Pub. No.: WO2013/040122
PCT Pub. Date: Mar. 21, 2013

(65) Prior Publication Data
US 2014/0341636 A1  Nov. 20, 2014

Related U.S. Application Data

(60) Provisional application No. 61/535,342, filed on Sep. 15, 2011.

(51) Int. Cl.
*A61C 17/34* (2006.01)
*A61C 17/22* (2006.01)

(52) U.S. Cl.
CPC .......... *A61C 17/222* (2013.01); *A61C 17/225* (2013.01); *A61C 17/3409* (2013.01);
(Continued)

(58) Field of Classification Search
CPC . A61C 17/34; A61C 17/3481; A61C 17/3409; A46B 13/02
(Continued)

(56) References Cited

U.S. PATENT DOCUMENTS 3,187,360 A  6/1965  Spohr
3,256,031 A  6/1966  Fillweber
(Continued)

FOREIGN PATENT DOCUMENTS

CH  391 652  5/1965
FR  2 276 015  1/1976
(Continued)

OTHER PUBLICATIONS

International Search Report and the Written Opinion issued in International Application PCT/US2012/054998 dated Mar. 27, 2013.
(Continued)

*Primary Examiner* — Michael Jennings

(57) ABSTRACT

A refill head (100), and oral care implement incorporating the same, wherein the refill head (100) can be uncoupled from a stem (220) of a handle (200) by withdrawing the refill head (100) from the stem of a handle (200) along the longitudinal axis of the oral care implement, which results in locking members (134) on the refill head (100) disengaging from an engagement rib (230) on the stem (220). The locking members (134) and engagement rib (230) may be aligned with or angled relative to the longitudinal axis of the oral care implement. A portion of the stem may be visible through a portion of the refill head to reinforce the proper connection between the refill head and the handle.

14 Claims, 13 Drawing Sheets

(52) U.S. Cl.
CPC ..... *A61C 17/3481* (2013.01); *Y10T 403/1624* (2015.01); *Y10T 403/608* (2015.01)

(58) Field of Classification Search
USPC .................................. 15/22.1, 176.1, 176.6
See application file for complete search history.

(56) References Cited

U.S. PATENT DOCUMENTS

| | | | |
|---|---|---|---|
| 3,400,417 A | | 9/1968 | Moret |
| 3,851,984 A | * | 12/1974 | Crippa ................... A61C 17/02 |
| | | | 15/176.6 |
| 4,991,249 A | * | 2/1991 | Suroff ................ A46B 15/0002 |
| | | | 15/176.2 |
| 5,365,627 A | * | 11/1994 | Jousson ............... A46B 5/0095 |
| | | | 15/176.6 |
| 5,381,576 A | * | 1/1995 | Hwang .............. A61C 17/3481 |
| | | | 15/22.1 |
| 5,461,744 A | | 10/1995 | Merbach |
| 5,617,601 A | * | 4/1997 | McDougall .......... A46B 13/008 |
| | | | 15/22.1 |
| 6,546,585 B1 | * | 4/2003 | Blaustein ............... A46B 5/026 |
| | | | 132/321 |
| 6,709,185 B2 | | 3/2004 | Lefevre |
| 7,690,067 B2 | | 4/2010 | Schaefer et al. |
| 7,857,623 B2 | | 12/2010 | Grez |
| 8,656,548 B2 | * | 2/2014 | Jungnickel ........... A61C 17/222 |
| | | | 15/159.1 |
| 2004/0016067 A1 | * | 1/2004 | Kraemer ............... A61C 17/222 |
| | | | 15/22.1 |
| 2010/0101032 A1 | | 4/2010 | Kressner |
| 2011/0072603 A1 | | 3/2011 | Vu et al. |
| 2011/0083288 A1 | * | 4/2011 | Kressner .............. A61C 17/222 |
| | | | 15/22.1 |
| 2011/0107536 A1 | | 5/2011 | Dabrowski et al. |

FOREIGN PATENT DOCUMENTS

| | | |
|---|---|---|
| FR | 2325335 | 4/1977 |
| FR | 2 476 994 | 9/1981 |
| KR | 20090082551 | 7/2009 |
| WO | WO 2005/046506 | 5/2005 |
| WO | WO 2011/079025 | 6/2011 |

OTHER PUBLICATIONS

Written Opinion of the International Preliminary Examining Authority issued in International Application PCT/US2012/054998 dated Aug. 11, 2013.

* cited by examiner

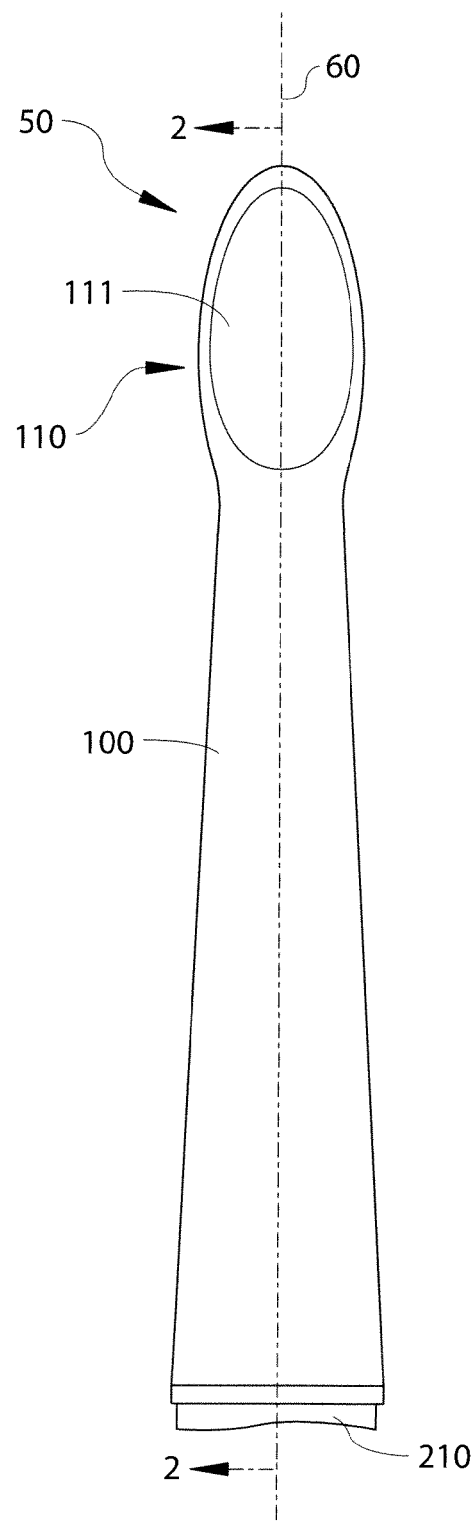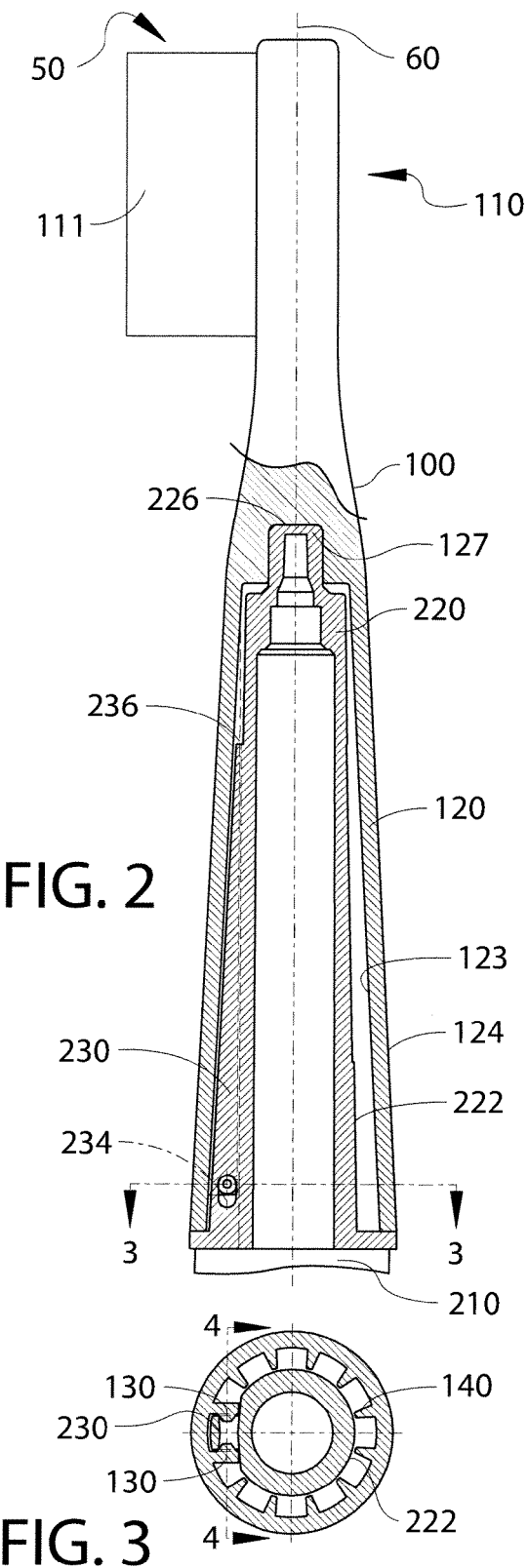

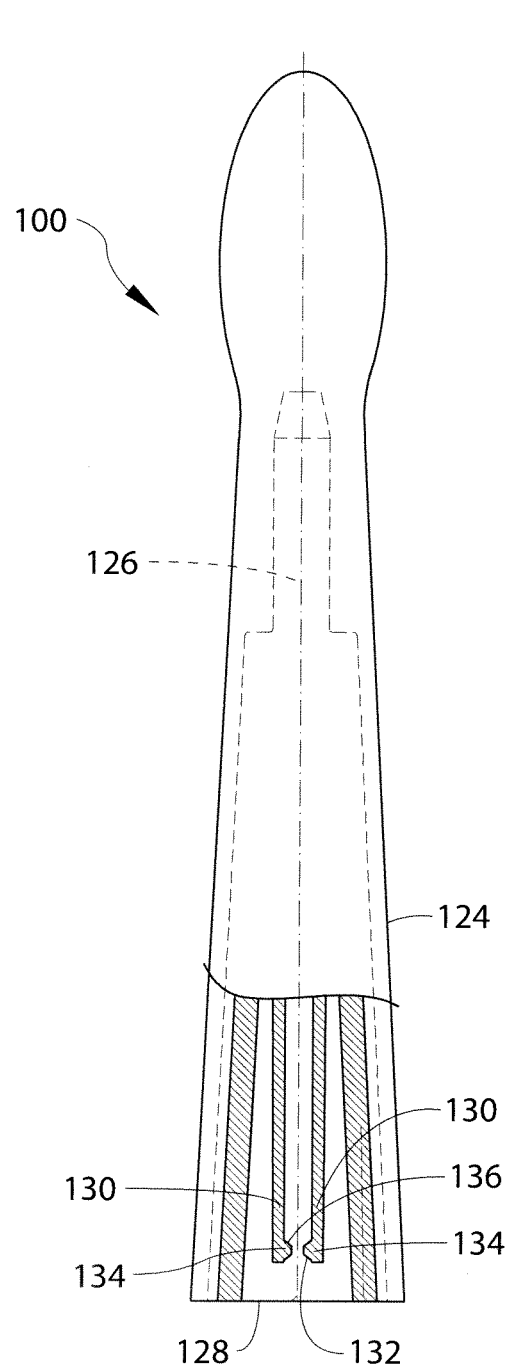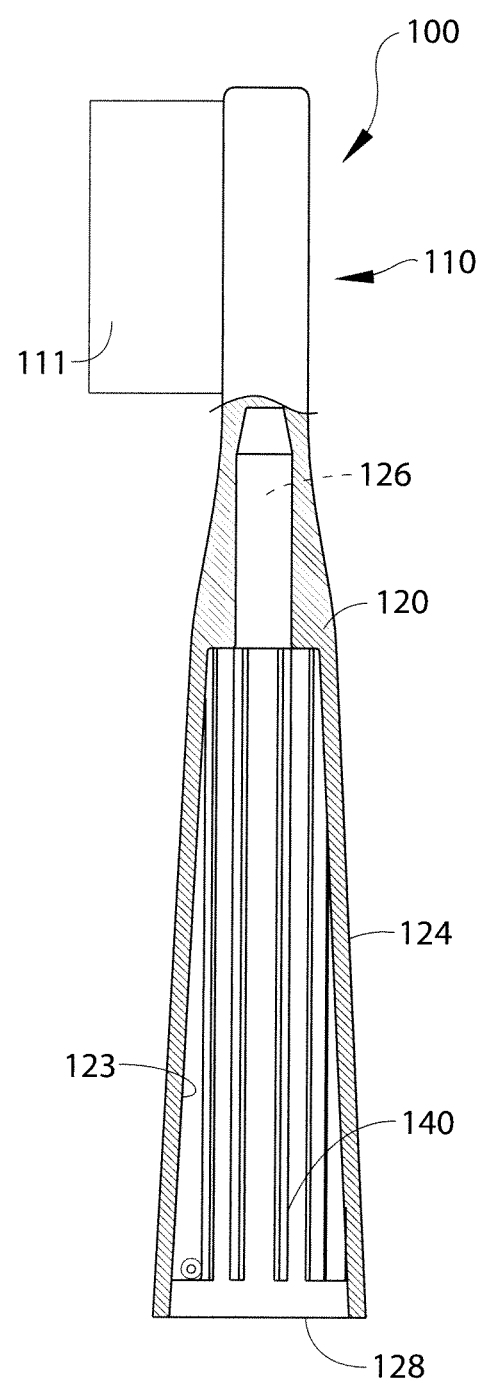
FIG. 8                    FIG. 9

ORAL CARE IMPLEMENT AND REFILL HEAD THEREFOR

CROSS-REFERENCE TO RELATED PATENT APPLICATIONS

The present application is a U.S. national stage application under 35 U.S.C. §371 of PCT Application No. PCT/US2012/054998, filed Sep. 13, 2012, which claims benefit to U.S. Provisional Application Ser. No. 61/535,342, filed Sep. 15, 2011, the entireties of which are incorporated herein by reference.

FIELD OF THE INVENTION

The present invention relates generally to refill heads for oral care implements, and specifically to the coupling structure of the refill head.

BACKGROUND OF THE INVENTION

Powered toothbrushes having replaceable heads, commonly referred to as refill heads, are known in the art. Such powered toothbrushes typically include a handle and a refill head that is detachably coupled to the handle. The replaceability of the heads in such powered toothbrushes is desirous because the handle, which includes the motion-inducing circuitry and components, is expensive to manufacture and has a much longer life expectancy than do the tooth cleaning elements, such as the bristles, that are on the refill head. It would be cost prohibitive to purchase such powered toothbrushes if they had to be discarded when the bristles or other cleaning elements wore out. Thus, it is now standard in the industry to provide refill heads that can be attached and detached from the handle so that worn out refill heads can be replaced as needed for the same handle.

Existing refill heads suffer from a number of deficiencies, including complexity of manufacture, the ability to improperly load the refill head to the handle, and inadequate coupling of the refill head to the handle. Thus, a need exists for a refill head having an improved coupling structure.

BRIEF SUMMARY OF THE INVENTION

The present invention is directed to a refill head, and oral care implement incorporating the same, wherein the refill head can be uncoupled from a stem of a handle by withdrawing the refill head from the stem of a handle along an axis of the oral care implement that results in locking members on the refill head disengaging from an alignment rib on the stem. A portion of the stem is preferably visible through a portion of the refill head to reinforce the proper connection between the refill head and the handle.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is one embodiment of a front view of a refill head and a toothbrush handle according to one embodiment of the present invention;

FIG. 2 is one embodiment of a partial cross-section taken along line 2-2 of FIG. 1;

FIG. 3 is one embodiment of a cross-section taken along line 3-3 of FIG. 2;

FIG. 8 is one embodiment of a partial rear cross-section of a brush head;

FIG. 9 is one embodiment of a partial side cross-section of a brush head;

DETAILED DESCRIPTION OF THE INVENTION

Figure 4:
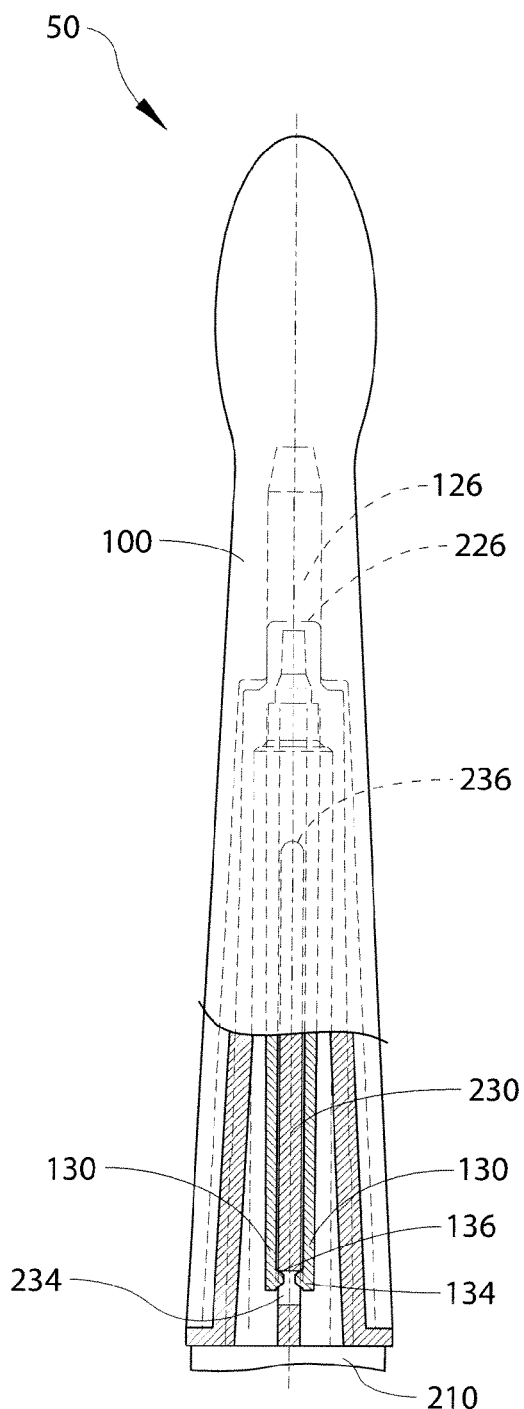
FIG. 4 is one embodiment of a partial cross-section taken along line 4-4 of FIG. 3, showing the locking engagement of a refill head with a toothbrush handle.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring to FIGS. 1 through 9 concurrently, a powered toothbrush 50 according to one embodiment is illustrated. The powered toothbrush 50 generally comprises a refill head 100, shown separately in FIGS. 8 and 9, and a handle portion 200 shown separately in FIGS. 6 and 7. The powered toothbrush 50 generally extends along a longitudinal axis 60 as shown in FIGS. 1 and 2. As discussed in greater detail below, the refill head 100 and the handle 200 are designed so that the refill head 100 can be repetitively coupled to and uncoupled from the handle 200. In FIGS. 1 through 4, the powered toothbrush 50 is illustrated in a state wherein the refill head 100 is coupled to the handle 200 according to an embodiment of the present invention, while in FIG. 5 the refill head 100 is not completely coupled to the handle 200 but is positioned in axial alignment with the handle 200 so that such coupling can be effectuated.

While the invention is exemplified herein as a powered toothbrush 50, it is to be understood that the inventive concepts discussed herein can be applied to a variety of oral care implements including, but not limited to, manual toothbrushes that utilize refill heads, or other manual or powered oral care implements, including without limitation tongue cleaners, water picks, interdental devices, tooth polishers and specially designed ansate implements having tooth engaging elements.

The refill head 100 generally comprises a head portion 110 and a sleeve 120 that is coupled to the head portion 110, the sleeve 120 further comprising an inner surface 123, an outer surface 124, a cavity 126 defined by the inner surface 123 and an opening 128 that provides access to such cavity 126. In the exemplified embodiment, the sleeve 120 and the head portion 110 of the refill head 100 are integrally fixated as a single unitary structure using a molding, milling, machining or other suitable process. However, in other embodiments the head portion 110 and the sleeve 120 of the refill head 100 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. When the refill head 100 is detachably coupled to the handle 200 in accordance with aspects of the present invention, a portion of the handle 200 is received into the cavity 126 through the opening 128 in the sleeve 120. The sleeve 120 and the head portion 110 of the refill head 100 are generally formed of a material that is rigid, such as a moldable hard plastic. Suitable hard plastics include polymers and copolymers of ethylene, propylene, butadiene, vinyl compounds and polyesters such as polyethylene terephthalate. Of course, the invention is not to be so limited and other materials can be used to form the sleeve 120 and head portion 110 of the refill head 100.

In the illustrated embodiment, the head portion 110 of the refill head 100 comprises a collection of oral cleaning elements such as tooth cleaning elements 111 extending therefrom for cleaning and/or polishing contact with an oral surface and/or interdental spaces. In the exemplified embodiment, the tooth cleaning elements 111 are generically illustrated. While the collection of tooth cleaning elements 111 is suited for brushing teeth, the collection of tooth cleaning elements 111 can also be used to polish teeth instead of or in addition to cleaning teeth. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 111 of the present invention can be connected to the refill head 100 in any manner known in the art. For example, staples/anchors, in-mold tufting (IMT) or anchor free tufting (AFT) could be used to mount the tooth cleaning elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

Referring now to FIGS. 1 through 7 concurrently, the handle 200 will be described in greater detail. The handle 200 generally comprises a gripping portion 210 (only a small portion of which is exemplified in the figures) and a stem 220. The stem 220 extends from the gripping portion 210 along the longitudinal axis 60. The gripping portion 210 of the handle 200 is typically an elongated structure that provides the mechanism by which a user can hold and manipulate the toothbrush 50 during use. The gripping portion 210 can take on a wide variety of shapes, contours and configurations, none of which are limiting of the present invention. Although not illustrated herein, it should be understood that included within the gripping portion 210 is preferably a power source, a motor, circuitry and components necessary to create a desired motion within the refill head 100 that is transmitted via the stem 220, such as vibratory motion, for example. The gripping portion 210 may also preferably include a user interface that controls the various operations of the toothbrush 50, including without limitation turning off and on, changing speeds of the motor, or other functions. The gripping portion 210 preferably forms a watertight housing for the aforementioned electrical circuit and mechanical components that need to be protected from moisture.

The stem 220 further comprises an outer surface 222, a base 224 and a distal end 226 that engages with the cavity 126 in the refill head 100 and that enables the refill head 100 to be repetitively coupled to and uncoupled from the handle 200 as will be described below. A rib 230, which is hereinafter referred to as an anti-rotation rib 230 for purposes of explanation, partially extends along the outer surface 222 of the stem 220 a distance 232 (FIG. 7) from the base 224 to a top 236 in the direction of the distal end 226 and tapers inwardly from the base 224 to the top 236 along such distance 232. In some embodiments, the rib 230 functions to rotatably index the refill head 100 relative to the handle 200 and stem 220 and prevent relative rotation thereof upon a secure attachment of the refill head 100 to the handle 200. The anti-rotation rib 230 further comprises an opening 234 for receiving and engaging a portion of the refill head 100 as will be described below. While the anti-rotation rib 230 is shown with certain dimensions having a certain structure, thickness and cross-section, it will be appreciated that other configurations are possible without departing from the scope of the present disclosure.

Returning to FIGS. 2 through 5, 8 and 9, the sleeve 120 further comprises a plurality of engagement ribs 130 circumferentially arranged around the inner surface 123 of the sleeve 120 that align on either side of anti-rotation rib 230 provided on the outer surface 222 of the stem 220 when the stem 220 is inserted into the cavity 126 of the refill head 100. As shown in FIG. 3, the sleeve 120 is also preferably provided with a plurality of inwardly directed alignment ribs 140 that facilitate the indexing and rotational alignment of the anti-rotation rib 230 with the engagement ribs 130 during the initial placement of the tubular sleeve 120 relative to the stem 220 (or vice versa). The engagement ribs 130 are also provided with locking members 134 (FIG. 8) that include a first cam surface 132 to facilitate engagement of the engagement ribs 130 with the opening 234 in the anti-rotation rib 230, and a second cam surface 136 to facilitate disengagement of the engagement ribs 130 with the opening 234.

Figure 5:
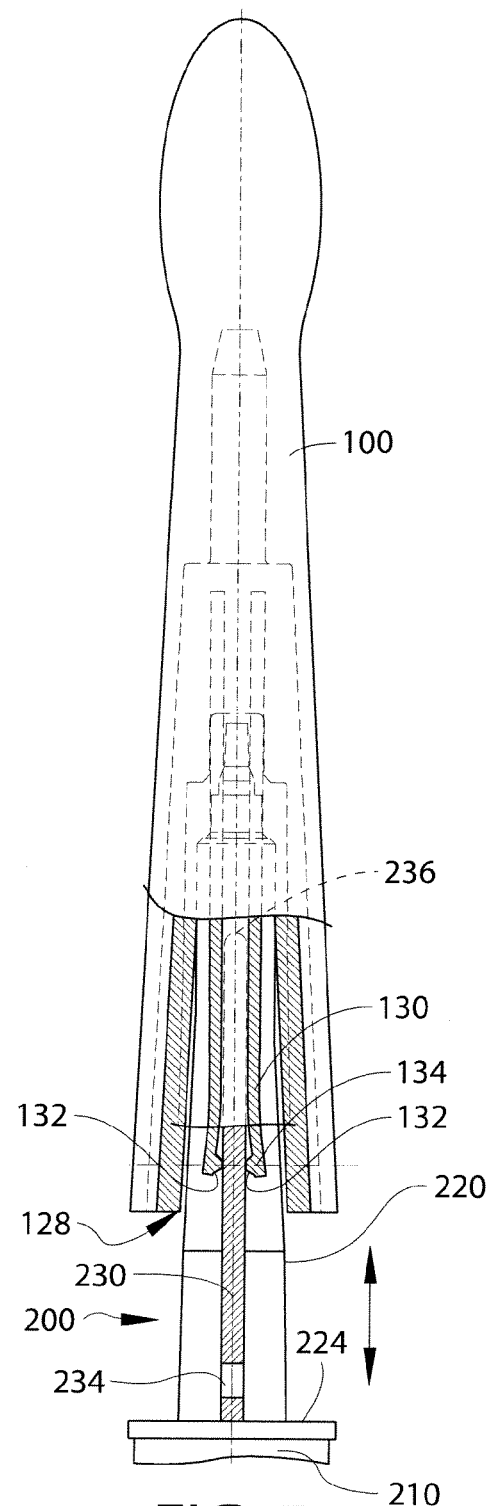
FIG. 5 is one embodiment of a partial cross-section similar to that of FIG. 4, showing the partial engagement of a refill head with a toothbrush handle.
Figure 6:
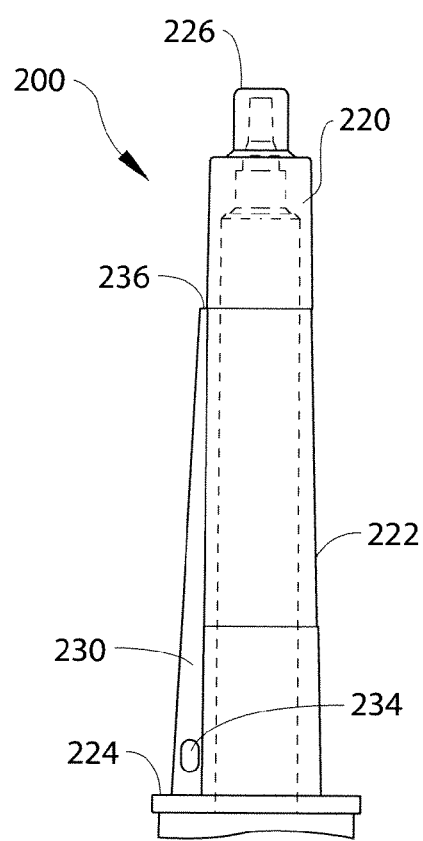
FIG. 6 is one embodiment of a side view of a toothbrush handle stem of the present disclosure.
Figure 7:
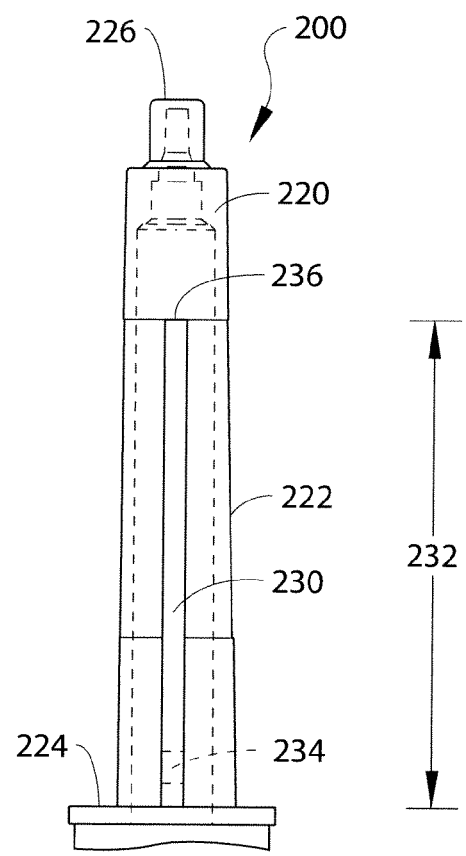
FIG. 7 is one embodiment of a front view of the handle of FIG. 6.
Figure 10:
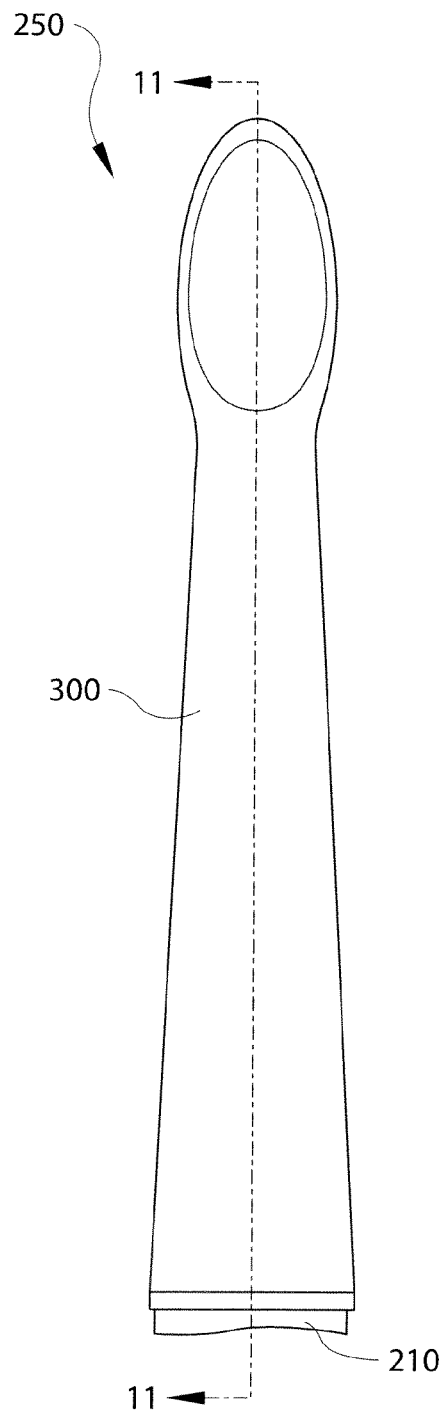
FIG. 10 is one embodiment of a front view of a refill head and a toothbrush handle according to one embodiment of the present invention.
Figure 11:
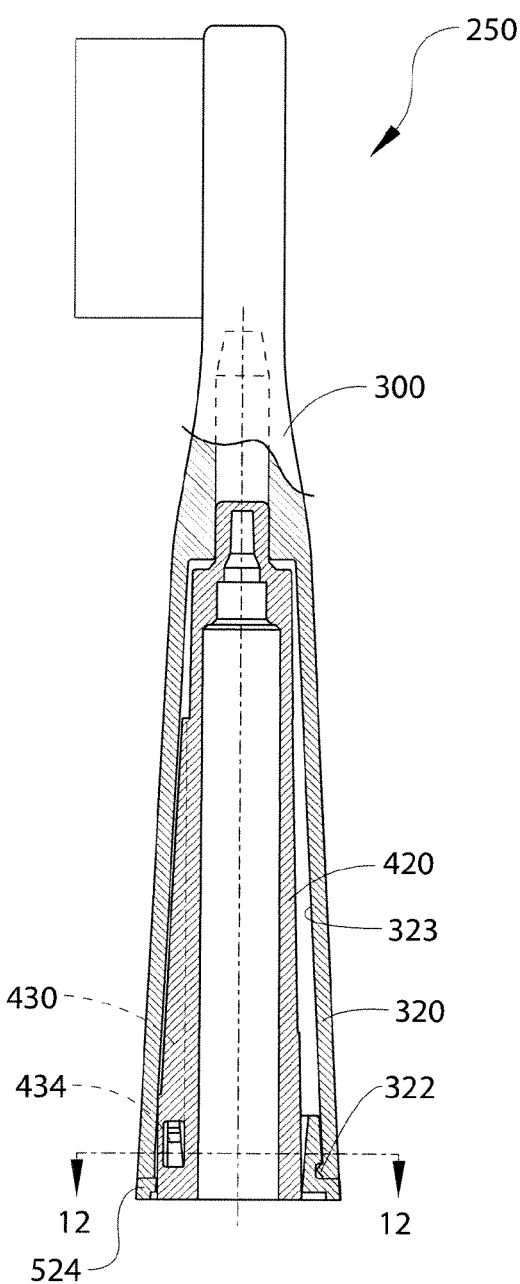
FIG. 11 is one embodiment of a partial cross-section taken along line 11-11 of FIG. 10.

More specifically as shown in FIGS. 4 and 5, during attachment of the refill head 100 to the stem 220 of the handle 200 and after the initial indexing and rotational alignment of the anti-rotation rib 230 with the engagement ribs 130, the impact of the first cam surfaces 132 against the top 236 of the anti-rotation rib 230 causes the engagement ribs 130 to flex outwardly as shown in FIG. 5 to accommodate the passage of the anti-rotation rib 230 through the outwardly flexed engagement ribs 130. After continued movement of the anti-rotation rib 230 through the outwardly flexed engagement ribs 130 and when the locking members 134 arrive at the opening 234 in the anti-rotation rib 230, the locking members 134 return to their original position (FIG. 8) by flexing inwardly and becoming seated within the opening 234 as shown in FIG. 4. Thus, the locking members 134 are movable relative to and engage with the opening 234 along a direction that is substantially perpendicular to the length or extension of the anti-rotation rib 230 along the stem 220, and that is also substantially perpendicular to the movement of the refill head 100 relative to the handle 200 during attachment and removal therefrom. The engagement of the locking members 134 from a substantially perpendicular direction and the positioning of the locking members 134 within the opening 234 function to secure the refill head 100 to the handle 200 and prevent relative rotation therebetween. When it is desired to remove the refill head 100 from the handle 200, a user simply needs to pull upward on the refill head 100 with sufficient force to urge the second cam surfaces 136 (FIG. 8) against the walls of the opening 234 to cause the locking members 134 and the engagement ribs 130 to flex outwardly and become released from the opening 234, and thereby enable the anti-rotation rib 230 to be drawn through the outwardly flexed engagement ribs 130 and the refill head 100 to be withdrawn from the handle 200.

In the embodiment of FIGS. 1-9, the engagement and disengagement of a refill head 100 relative to a handle 200 occurs solely through a vertical movement or a movement along the longitudinal axis 60 of the toothbrush 50. With the engagement mechanism of the present disclosure, only the relative movement of the locking members 134 relative to the anti-rotation rib 230 along the longitudinal axis 60 is necessary to create sliding movement and repeatable coupling therebetween.

In addition, the stem 220, when assembled to the refill head 100, is in intimate contact with the upper portion 127 of the cavity 126 as shown in FIG. 2 for purposes of maximizing the transmission of energy and/or movement (such as vibration, for example) from the stem 220 to the refill head 100. However, as shown in FIG. 2, the contact between the stem 220 and the refill head 100 below the upper portion 127 of the cavity 126 is minimized to the contact between the anti-rotation rib 230 with the engagement ribs 130 and the contact between the stem 220 and the tips of the alignment ribs 140. Thus, the transmission of energy from the stem 220 to the handle 200 and subsequently to a user (not shown) holding the handle is minimized.

In the embodiment of FIGS. 1-9, the stem 220 is indexed and secured relative to the refill brush head 100 by the engagement of the anti-rotation rib 230 on the stem 220 with the engagement ribs 130 extending from the inner surface 123 of the sleeve 120. Thus, relative secured alignment and movement is achieved through an inter-engagement between only the handle 200 and the brush head 100. In an alternative embodiment of FIGS. 10-16 collectively, there is provided a toothbrush 250 having a refill head 300 and a handle 400, the handle 400 incorporating a stem 420 having a rib 430 that functions as an anti-rotation rib 430 with an opening 434 as shown in FIGS. 13-16, similar to the embodiment of FIGS. 1-9. However, instead of having a portion of the refill head 300 function to index and secure the refill head 300 relative to the stem 420 of the handle 400, a separate insert 500 (FIG. 16) is attached to the refill head 300 that creates a similar functionality with respect to indexing and securing the refill head 300 relative to the handle 400.

Figure 12:
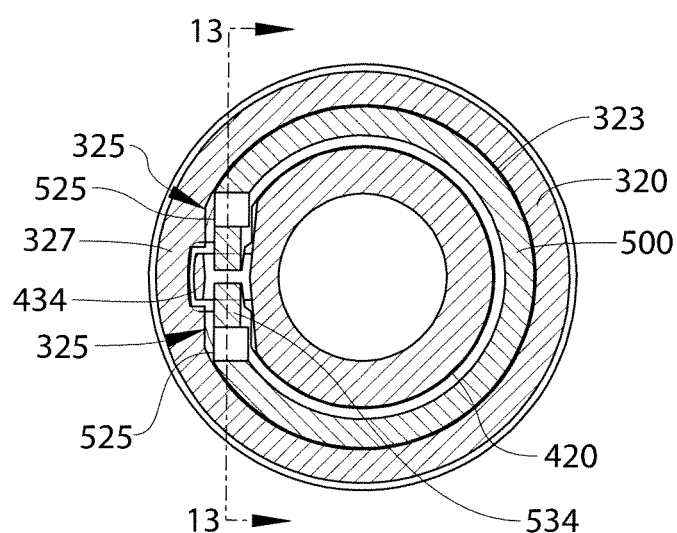
FIG. 12 is one embodiment of a cross-section taken along line 12-12 of FIG. 11.

Specifically, insert 500 comprises a circumferential groove 510 that engages an undercut bead 322 (FIG. 11) in an outer sleeve 320 of the refill head 300 that enables the press a snap fit engagement of the insert 500 with the outer sleeve 320. The outer sleeve 320 further comprises an inner surface 323 with two interior flat surfaces 325 (FIG. 12) that create a channel 327 therebetween to receive, index and align the anti-rotation rib 430 of the stem 420 with the outer sleeve 320 of the brush head 300. The insert 500 is also provided with a plurality of flat wall portions 525 (FIGS. 12 and 16) that are aligned with the flat surfaces 325 on the inner surface 323 of the outer sleeve 320 that function to also index and align the insert 500 with the inner surface 323 of the outer sleeve 320 during the press engagement of the insert 500 with the outer sleeve 320 as discussed above. These flat wall portions 525 truncate the generally cylindrical shape of the insert 500 to form a "D" shape in the plan view as shown in FIG. 12. Thus, the insert 500 is preferably assembled relative to the outer sleeve 320 by first rotating the insert 500 relative to the sleeve 320 until the flat wall portions 525 of the insert 500 are aligned with the flat surfaces 325 on the inner surface 323 of the outer sleeve 320, whereupon the insert 500 is pressed into engagement with the sleeve 320 until the bead 322 on the sleeve 320 locks into the groove 510 on the insert 500 achieving a snap fit.

Figure 13:
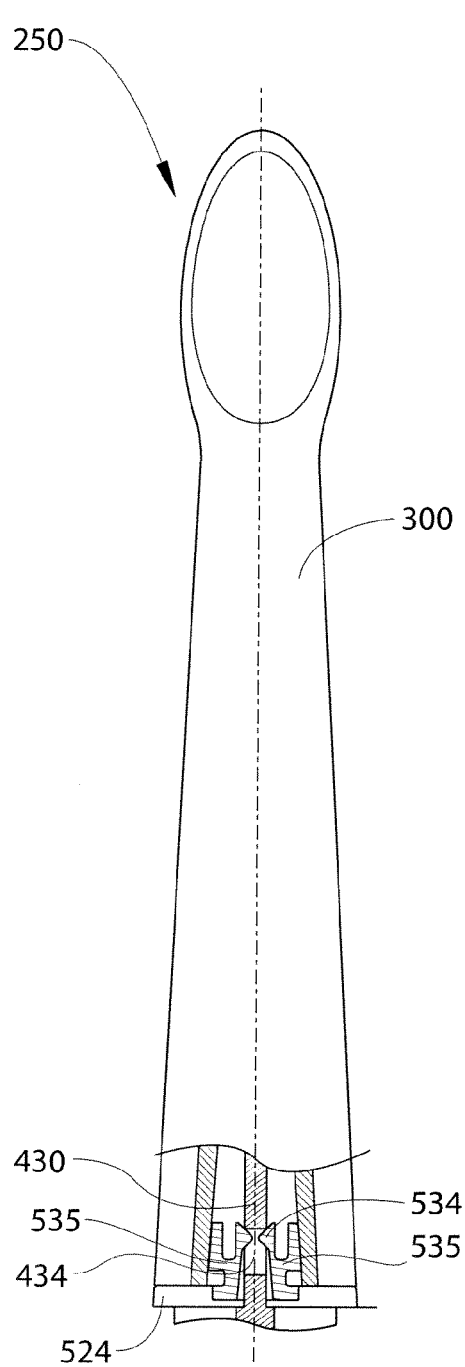
FIG. 13 is one embodiment of a partial cross-section taken along line 13-13 of FIG. 12 showing the locking engagement of a refill head with a toothbrush handle.
Figure 14:
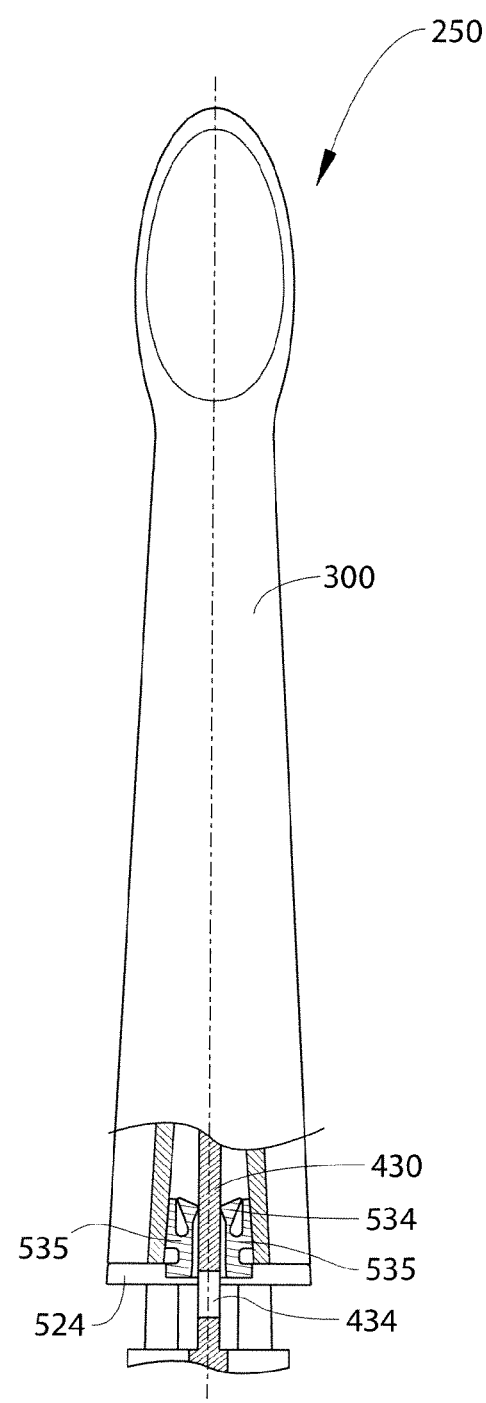
FIG. 14 is one embodiment of a partial cross-section similar to that of FIG. 13, showing the partial engagement of a refill head with a toothbrush handle.
Figure 15:
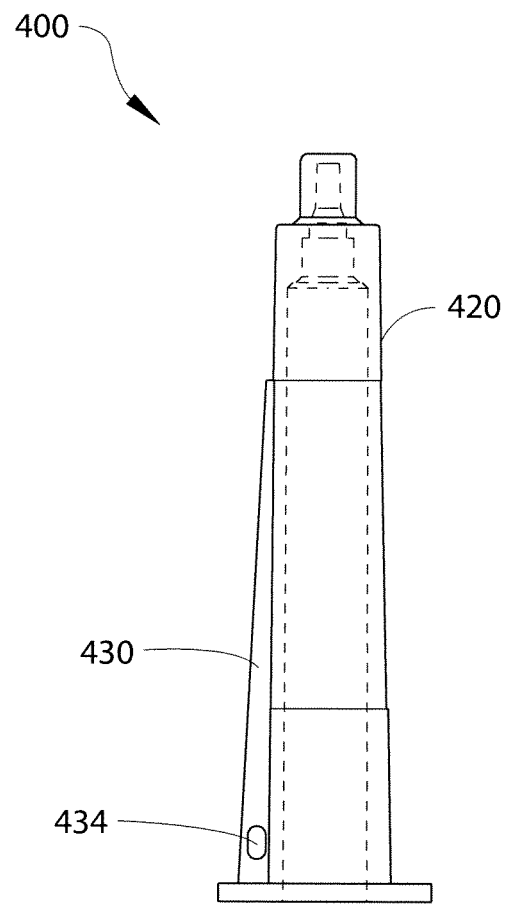
FIG. 15 is one embodiment of a side view of a toothbrush handle stem.
Figure 16:
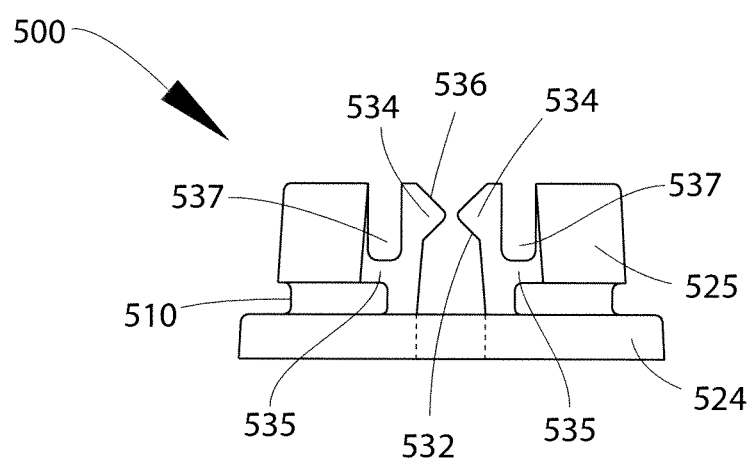
FIG. 16 is one embodiment of a diagrammatic view of an insert.
Figure 17:
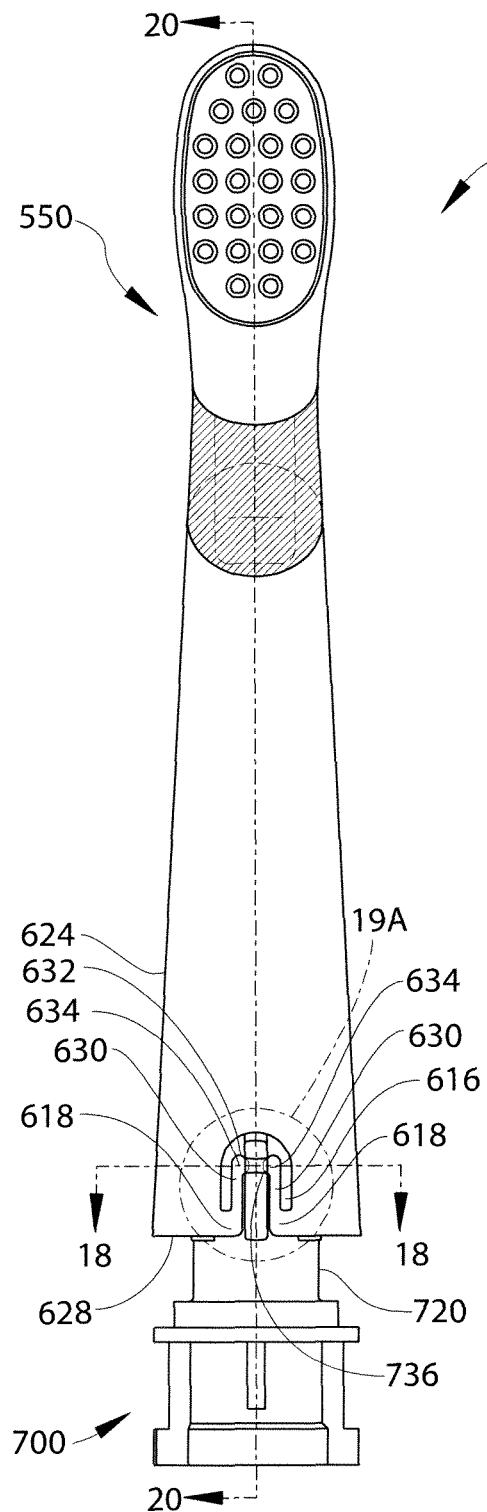
FIG. 17 is one embodiment of a front view of a refill head and a toothbrush handle according to another embodiment of the present invention.

The insert 500 further comprises, in the area of the flat wall portions 525, a plurality of resiliently-arranged locking members 534 that flex, by virtue of bridge members 535 and gaps 537, away from and toward each other and that have first and second cam surfaces 532 and 536 (FIG. 16) that engage the anti-rotation rib 430 and the opening 434 in such rib 430 as shown in FIGS. 13 and 14 in a similar manner as the locking members 134 engage opening 234 of anti-rotation rib 230 in the embodiment of FIGS. 4 and 5. Specifically, after the outer sleeve 320 has been rotated relative to the stem 420 and the anti-rotation rib 430 has been aligned within the channel 327 formed by the flat surfaces 325 on the inner surface 323 of the outer sleeve 320, the anti-rotation rib 430 is advanced against the first cam surface 532 causing the locking members 534 to spread apart (FIG. 14) until the anti-rotation rib 430 is advanced far enough that the locking members 534 flex back into seating engagement with the opening 434 as shown in FIG. 13. The locking members 534 are thus similarly movable relative to and engage with the opening 434 along a direction that is substantially perpendicular to the length or extension of the anti-rotation rib 430 along the stem 420. The engagement of the locking members 534 from a substantially perpendicular direction and the positioning of the locking members 534 within the opening 434 function to secure the refill head 300 to the handle 400 and prevent relative rotation therebetween. When it is desired to remove the refill head 300 from the handle 400, a user simply needs to pull upward on the refill head 300 with sufficient force to urge the second cam surfaces 536 against the walls of the opening 434 to cause the locking members 534 to flex outwardly and become released from the opening 434, and thereby enable the anti-rotation rib 430 to be completely drawn through the outwardly flexed locking members 534 until the refill head 300 is withdrawn from the handle 400.

In the illustrated embodiment, the insert 500 is also provided with a protruding cylindrical bottom wall 524 which, when molded in a different color from the outer sleeve 320, provides a unique visual identifier for distinguishing between more than one user of the toothbrush 250. In other words, different users (not shown) may designate different toothbrushes by the color of the bottom wall, such that a user may associate his or her brush head with a particular insert, which would prevent cross contamination amongst different users.

In yet another embodiment illustrated in FIGS. 17-22 collectively, there is provided a toothbrush 550 having a refill head 600 and a handle 700, the refill head having an attachment axis 660 (FIG. 20), a sleeve 620 formed from a wall 622 and having an inner surface 623, an outer surface 624, an opening 628 that defines an internal cavity 626 for receiving the handle 700, the handle 700 incorporating a stem 720 having a rib 730 that functions as an anti-rotation rib 730 with an opening 734, similar to the embodiment of FIGS. 1-9. However, instead of having engagement ribs 130 arranged around the inner surface 123 of the sleeve 120 as shown in FIGS. 1-9, there are provided engagement ribs 630 integral with a wall 622 of the sleeve 620 that resiliently engage the opening 734 of the anti-rotation rib 730 that creates a similar functionality with respect to indexing and securing the refill head 600 relative to the handle 700. In addition, a portion of the anti-rotation rib 730 is exposed or visible through the sleeve 620 when the refill head 600 is attached to the handle stem 720, which reinforces to the user the proper connection between the refill head 600 and the handle stem 720.

Figure 18:
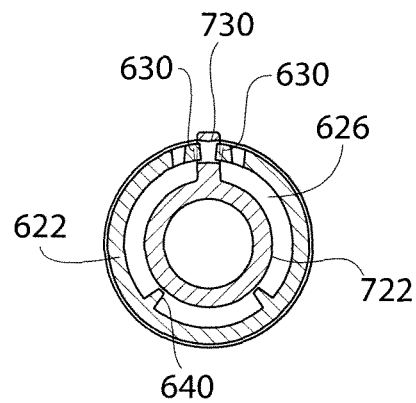
FIG. 18 is one embodiment of a cross-section taken along line 18-18 of FIG. 17.
Figure 21:
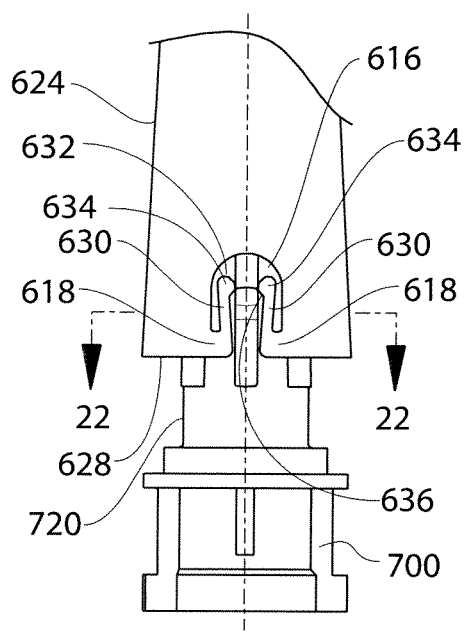
FIG. 21 is one embodiment of a close-up of the intersection between the refill head and toothbrush handle of FIG. 17.
Figure 22:
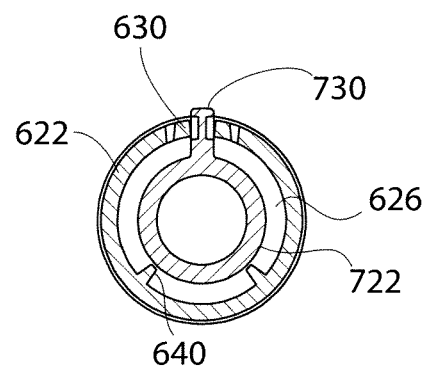
FIG. 22 is one embodiment of a cross-section taken along line 22-22 of FIG. 21.

Specifically, the plurality of engagement ribs 630 are circumferentially arranged around the wall 622 of the sleeve 620 and align on either side of anti-rotation rib 730 provided on the outer surface 722 of the stem 720 when the stem 720 is inserted into the cavity 626 of the refill head 600. The plurality of engagement ribs 630 extend upwardly from the opening 628 and are spaced from each other by a second opening 610 in the wall 622 having a first section 612 defined along an engagement axis 614 between the plurality of engagement members 630, and a second section 616 that partially surrounds the plurality of engagement members 630 and that enables the plurality of engagement members 630 to move, via bridges 618 defined in the wall 622 adjacent the opening 628, relative to the engagement axis 614 and relative to the wall 622 of the sleeve 620. The combination of the first linear section 612 and the second curved section 616 of the second opening 610 form the appearance of an umbrella around the resilient engagement members 630. The first section 612 of the second opening 610 also functions to index the anti-rotation rib 730 and the handle 700 relative to the refill head 600 as the anti-rotation rib 730 partially resides within the first section 612 of the second opening 610 during engagement of the refill head 600 with the handle 700. In addition, the second opening 610 functions to expose a portion of the anti-rotation rib 730 through the sleeve 620 when the refill head 600 is attached to the handle stem 720, which reinforces to the user the proper connection between the refill head 600 and the handle stem 720. As shown in FIGS. 18 and 21, the sleeve 620 is also preferably provided with a plurality of inwardly directed alignment ribs 640 that facilitate the indexing and rotational alignment of the anti-rotation rib 730 with the engagement ribs 630 during the initial placement of the sleeve 620 relative to the stem 720 (or vice versa). The engagement ribs 630 are also provided with locking members 634 (FIG. 19A) that include a first cam surface 632 to facilitate disengagement of the engagement ribs 630 with the opening 734 in the anti-rotation rib 730, and a second cam surface 636 to facilitate engagement of the engagement ribs 630 with the opening 734.

Figure 19A:
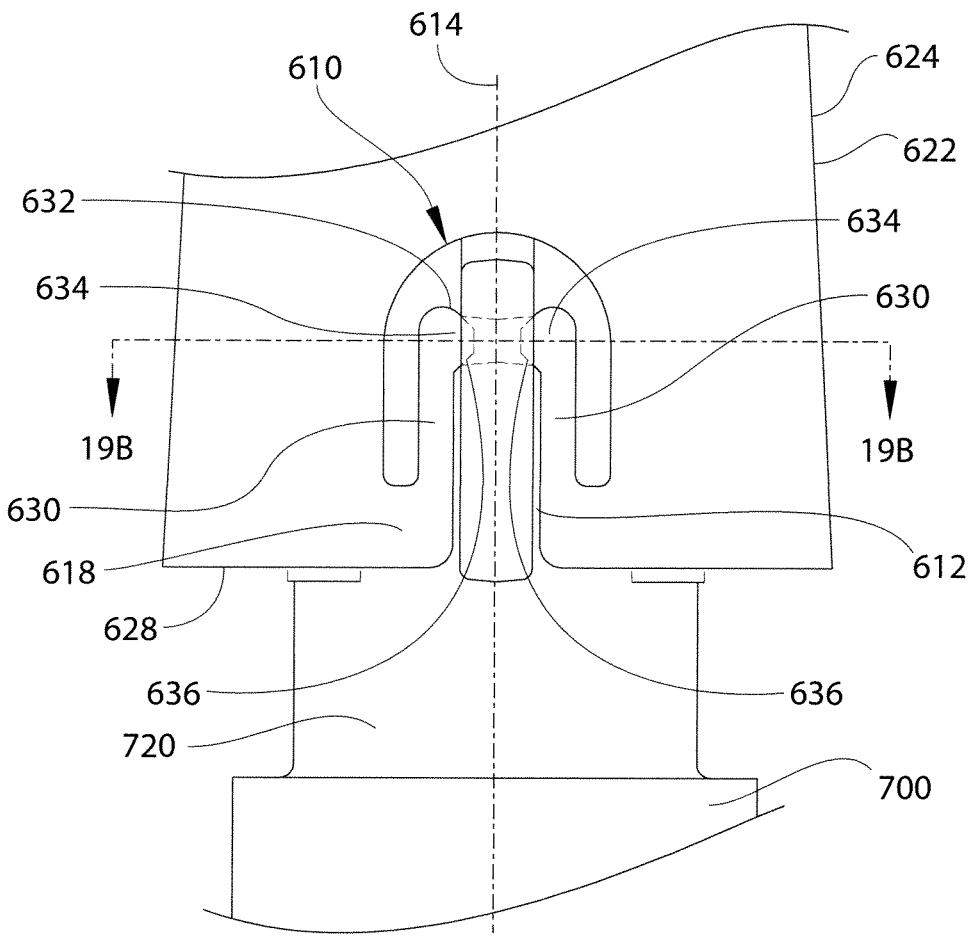
FIG. 19A is one embodiment of a close-up view taken along circle 19A of FIG. 17.
Figure 19B:
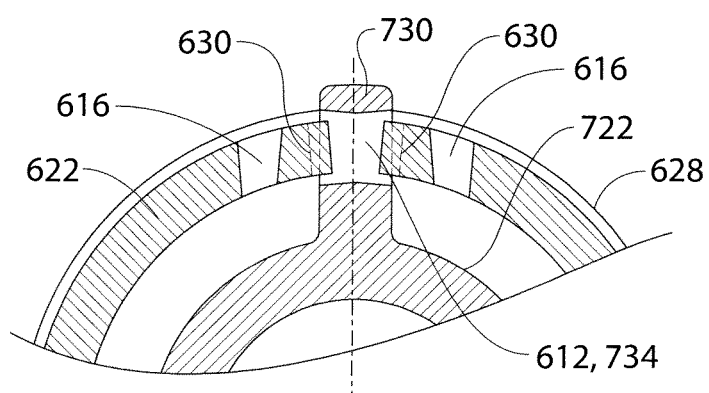
FIG. 19B is one embodiment of a cross-section taken along line 19B-19B of FIG. 19A.

More specifically, during attachment of the refill head 600 to the stem 720 of the handle 700 and after the initial indexing and rotational alignment of the anti-rotation rib 730 with the engagement ribs 630 and passage of the anti-rotation rib 730 into the first section 612 of the second opening 610 along the engagement axis 614, the impact of the second cam surfaces 636 against the top 736 (FIG. 20) of the anti-rotation rib 730 causes the engagement ribs 630 to flex outwardly into the second section 616 of the second opening 610 as shown in FIG. 21 to accommodate the passage of the anti-rotation rib 730 through the outwardly flexed engagement ribs 630. The engagement ribs 630 move relative to the wall 622 of the sleeve 620 by pivoting about the bridges 618 defined between the ribs 630 and the remainder of the sleeve 620. After continued movement of the anti-rotation rib 730 along the engagement axis 614 through the outwardly flexed engagement ribs 630, and when the locking members 634 arrive at the opening 734 in the anti-rotation rib 730, the locking members 634 return to their original position by flexing inwardly and becoming seated within the opening 734 as shown in FIGS. 19A and 19B. The user is also assured of a proper seating of the refill head 600 on the handle stem 720 through the exposure of a portion of the anti-rotation rib 730 through a portion of the wall 622 of the sleeve 620, and more specifically through the second opening 610 in the sleeve 620, when the refill head 600 is properly seated on the handle stem 720.

Thus, the locking members 634 are movable relative to and engage with the opening 734 along a direction that is substantially perpendicular to the engagement axis 614 and the length or extension of the anti-rotation rib 730 along the stem 720, and that is also substantially perpendicular to the movement of the refill head 600 relative to the handle 700 along the attachment axis 660 (FIG. 20) during attachment and removal therefrom. The engagement of the locking members 634 from a substantially perpendicular direction and the positioning of the locking members 634 within the opening 734 function to secure the refill head 600 to the handle 700 and prevent relative rotation therebetween. When it is desired to remove the refill head 600 from the handle 700, a user simply needs to pull upward on the refill head 600 along the attachment axis 660 with sufficient force to urge the first cam surfaces 632 (FIG. 19A) against the walls of the opening 734 to cause the locking members 634 and the engagement ribs 630 to flex outwardly and become released from the opening 734, and thereby enable the anti-rotation rib 730 to be drawn through the outwardly flexed engagement ribs 630 and the refill head 600 to be withdrawn from the handle 600. While not specifically shown, the anti-rotation rib 730 can be provided with depressions (not shown) on either side of the anti-rotation rib 730 that are engaged by the locking members 634 instead of an opening 734 extending through the anti-rotation rib 730. Other manners of engagement are possible.

Figure 20:
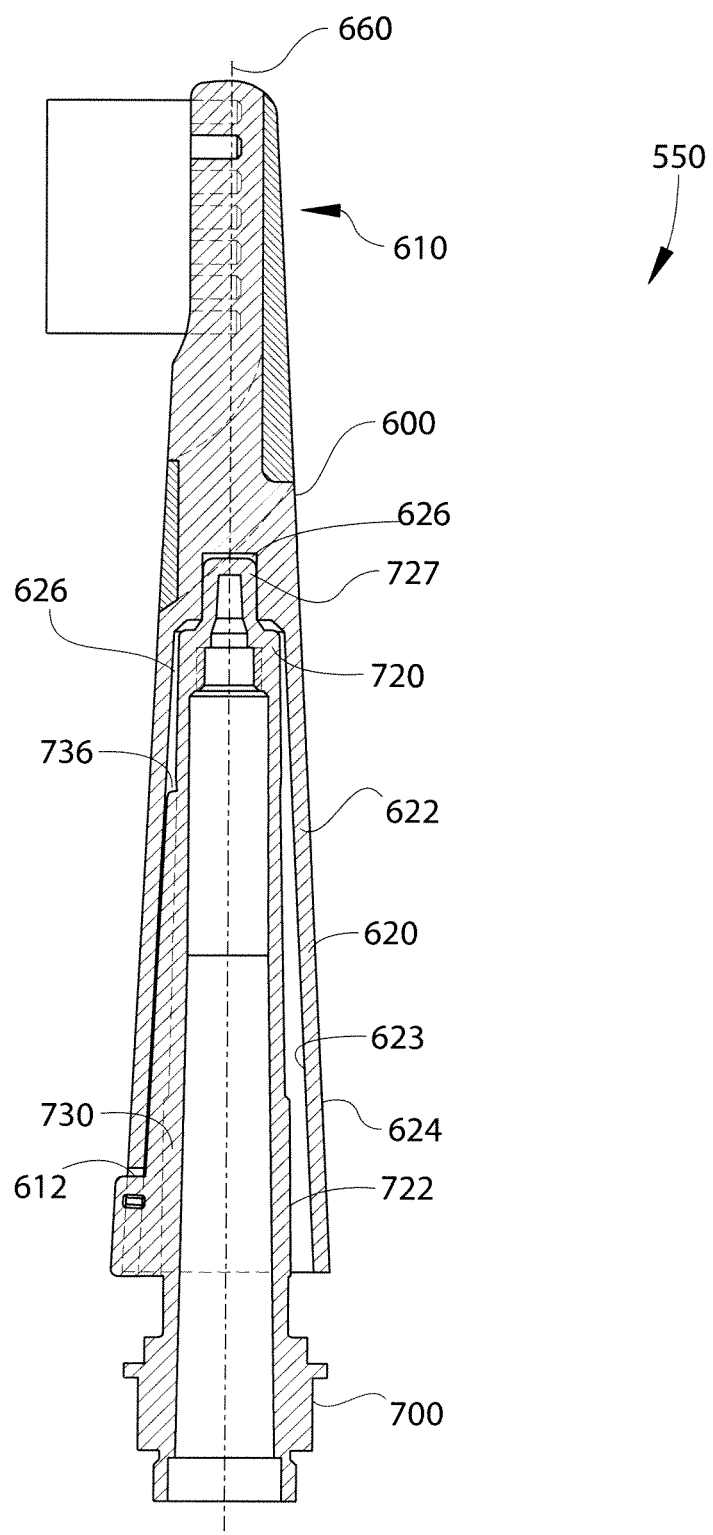
FIG. 20 is one embodiment of a partial cross-section taken along line 20-20 of FIG. 17.

In addition, the distal end 727 of the stem 720, when assembled to the refill head 600, is in intimate contact with the upper portion 627 of the cavity 626 as shown in FIG. 20 for purposes of maximizing the transmission of energy and/or movement (such as vibration, for example) from the stem 720 to the refill head 600. However, as shown in FIG. 18, the contact between the stem 720 and the refill head 600 below the upper portion 627 of the cavity 626 is minimized to the contact between the anti-rotation rib 730 with the engagement ribs 630 and the contact between the stem 720 and the tips of the alignment ribs 640. Thus, the transmission of energy from the stem 720 to the handle 700 and subsequently to a user (not shown) holding the handle is minimized.

In the embodiment of FIGS. 17-22, the engagement and disengagement of a refill head 600 relative to a handle 700 occurs solely through a vertical movement or a movement along the attachment axis 660 of the toothbrush 550. With the engagement mechanism of the present disclosure, only the relative movement of the locking members 634 relative to the anti-rotation rib 730 along the longitudinal or attachment axis 660 is necessary to create sliding movement and repeatable coupling therebetween.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. A refill head for an oral care implement having a handle stem, comprising:
   a) a sleeve having an attachment axis, a first opening and a wall defining a cavity for receiving the handle stem;
   b) a plurality of resilient engagement members arranged around the wall and extending upwardly relative to the first opening for engaging the handle stem, the plurality of resilient engagement members extending along an engagement axis; and
   c) opposing locking members provided on the engagement members, each locking member further comprising a first cam surface to facilitate engagement of the engagement members with the handle stem when the engagement members are aligned on either side of the handle stem, and a second cam surface to facilitate disengagement of the engagement members with the handle stem;
   wherein the sleeve further comprises a second opening partially surrounding the resilient engagement members into which the resilient engagement members move during engagement of the refill head with the handle stem, the second opening extending upwardly along the wall from the first opening and further comprising a first linear section extending along the engagement axis for receiving a portion of the handle stem and a second curved section attached to the first linear section that partially surrounds the resilient engagement members.

2. The refill head of claim 1, wherein the resilient engagement members are configured to spread apart during the engagement and disengagement of the refill head with the handle stem.

3. The refill head of claim 2, wherein the resilient engagement members are configured to approach each other while the refill head is engaged with the handle stem.

4. The refill head of claim 1, wherein the resilient engagement members are integral with the wall.

5. The refill head of claim 1, wherein the first linear section and second curved sections form the appearance of an umbrella around the resilient engagement members.

6. The refill head of claim 5, wherein the second opening defines bridges adjacent the resilient engagement members.

7. The refill head of claim 6, wherein the resilient engagement members are configured to pivot about the bridges during engagement of the refill head with the handle stem.

8. The refill head of claim 1, further comprising a plurality of alignment ribs circumferentially arranged around an inner wall of the sleeve.

9. An oral care implement comprising:
   a) a handle stem and a refill head having a sleeve coaxially aligned with the handle stem;
   b) the sleeve having an attachment axis, a first opening and a wall defining a cavity for receiving the handle stem;
   c) a plurality of resilient engagement members arranged around the wall for engaging the handle stem, the plurality of resilient engagement members extending along an engagement axis; and
   d) opposing locking members provided on the engagement members, each locking member further comprising a first cam surface to facilitate engagement of the engagement members with the handle stem when the engagement members are aligned on either side of the handle stem, and a second cam surface to facilitate disengagement of the engagement members with the handle stem;
   wherein the handle stem further comprises an engagement rib having an aperture that extends through the engagement rib from a first side of the engagement rib to a second side of the engagement rib, the aperture engaged by the resilient engagement members.

10. The oral care implement of claim 9, wherein the engagement rib extends along the handle stem in a first direction aligned with the engagement axis and the resilient engagement members engage the aperture in the engagement rib from a second direction that is substantially perpendicular to the first direction.

11. The oral care implement of claim 9, wherein the engagement rib tapers outwardly relative to the attachment axis.

12. The oral care implement of claim 9, wherein the resilient engagement members are configured to spread apart during the engagement and disengagement of the refill head with the handle stem, and are configured to approach each other while the refill head is engaged with the handle stem.

13. A refill head for an oral care implement having a handle stem, comprising:
   a) a sleeve comprising an attachment axis, a first opening, and a wall having an outer surface and an inner surface that defines a cavity for receiving the handle stem;
   b) a plurality of resilient engagement members extending from the inner surface of the wall into the cavity for engaging the handle stem, the plurality of resilient engagement members extending along an engagement axis; and
   c) opposing locking members provided on the engagement members, each locking member further comprising a first cam surface to facilitate engagement of the engagement members with the handle stem when the engagement members are aligned on either side of the handle stem, and a second cam surface to facilitate disengagement of the engagement members with the handle stem;
   wherein the resilient engagement members are integral with the wall.

14. The refill head of claim 13, wherein the first and second cam surfaces of each of the locking members are oblique to the attachment axis.

* * * * *